United States Patent [19]

Koeniger

[11] Patent Number: 5,507,805
[45] Date of Patent: Apr. 16, 1996

[54] INTRAOCULAR LENS AND METHOD OF RETAINING IN PLACE

[75] Inventor: Erich A. Koeniger, Metairie, La.

[73] Assignee: American Cyanamid Company, Wayne, N.J.

[21] Appl. No.: 885,322

[22] Filed: Jul. 14, 1986

Related U.S. Application Data

[63] Continuation of Ser. No. 610,717, May 16, 1984, abandoned, which is a continuation-in-part of Ser. No. 373,935, May 3, 1982, Pat. No. 4,449,257.

[51] Int. Cl.$^6$ .................................................. A61F 2/16
[52] U.S. Cl. .................................................. 623/6
[58] Field of Search .................................................. 623/6

[56] References Cited

U.S. PATENT DOCUMENTS

| | | | |
|---|---|---|---|
| 4,418,431 | 12/1983 | Feaster | 623/6 |
| 4,449,257 | 5/1984 | Koeniger | 623/6 |

FOREIGN PATENT DOCUMENTS

| | | |
|---|---|---|
| 1035877 | 7/1966 | United Kingdom. |
| 1391438 | 4/1975 | United Kingdom. |
| 1495043 | 12/1977 | United Kingdom. |
| 1534607 | 12/1978 | United Kingdom. |
| 2010865 | 7/1979 | United Kingdom. |
| 2010864 | 7/1979 | United Kingdom. |
| 1569493 | 6/1980 | United Kingdom. |
| 2119957 | 11/1983 | United Kingdom. |
| WO8100570 | 3/1981 | WIPO. |

OTHER PUBLICATIONS

Computer Search attached to application E. C. 25068208 Golbor et al Dep. Materials Sci. Eng. Gainsville, Fla.
Patent Office Scientific printout 25068209 Am. Chemical Society meeting; Las Vegas, Nev. Mar. 28, 1982 Goldberg E. P. et al.
Mehta, et al., "The New Soft Intraocular Lens Implant," *Am. Intra–Ocular Implant Soc. J.*, vol. IV, pp. 200–205, Oct. 1978.
Refolo, "Polymers in Ophthalmic Surgery," *J. Biomed. Mater. Res.*, vol. 5, pp. 113–119 (1971).

*Primary Examiner*—David Isabella
*Attorney, Agent, or Firm*—Scully, Scott, Murphy & Presser

[57] ABSTRACT

Intraocular lenses of non-rigid material are disclosed. In one embodiment, an intraocular lens of HEMA plastic or other soft plastic is cut to a size that is small for emplacing but fills the capsular bag of an eye after it has been emptied of its natural contents. The softening and expanding of a hydrophilic lens is caused by the aqueous humor uptake into the dry lens from the capsule environment. Means such as concentric grooves are also disclosed which engage the rough interior walls of the capsular bag to position and retain the lens in place.

29 Claims, 3 Drawing Sheets

INTRAOCULAR LENS AND METHOD OF RETAINING IN PLACE

CROSS REFERENCE TO RELATED APPLICATIONS

This application is a file wrapper continuation of my prior application Ser. No. 610,717, filed May 16, 1984 and now abandoned, which in turn is a continuation-in-part application of my prior application Ser. No. 373,935, filed May 3, 1982, and now U.S. Pat. No. 4,449,257.

BACKGROUND OF THE INVENTION

The invention relates generally to intraocular lenses and more particularly to a soft intraocular lens. It also relates to a method of retaining an intraocular lens in a posterior chamber capsule.

The prior art teaches hard PMMA or glass intraocular lenses that are held in place in the posterior chamber with loops, clips, staves and/or sutures.

SUMMARY OF THE INVENTION

The present invention teaches a soft plastic lens made for instance of HEMA (hydroxyethyl methacrylate) or a copolymer of HEMA or one or more comonomers, that is cut and shaped when dry to a shape that will expand and soften with the uptake of aqueous humor in the eye to fill the capsular bag of the eye. Alternatively, the lens is made of swollen hydrophilic plastic, or other soft, non-hydrophilic plastic. The lens can be held in place therein by means such as concentric grooves cut in the marginal peripheral area to frictionally engage rough interior surfaces of the capsule.

It is an object of the invention to provide a soft intraocular lens for placing in the capsular bag of the eye while hard that will soften and expand to fill the capsule. It is a further object to provide an intraocular lens which is soft before it is inserted into the capsular bag.

Another object of the invention is to form or cut concentric grooves or other means in the body of the lens, around the peripheral marginal areas, that will frictionally engage rough inner surfaces of the capsule when the lens softens and expands to fill the capsular bag on uptake of aqueous humor in the eye, regardless of whether the lens has other positioning means.

DETAILED DESCRIPTION OF THE INVENTION

Figure 1:
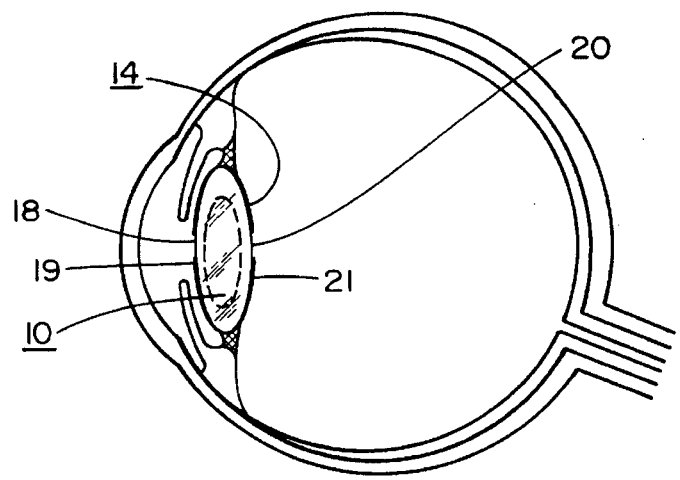
FIG. 1 is a vertical cross-section of an eye showing a lens of the invention operably in place dry and after aqueous humor uptake.

The present invention, as indicated, includes intraocular lenses which are non-rigid when they are in contact with the aqueous humor in the capsular bag of the patient. Thus, the invention includes lenses which are hard when they are first inserted, and which swell and soften after insertion. The invention also includes lenses which are made of material which is capable of such swelling and softening from an initial hard state, and which are in the swollen, non-rigid state before they are inserted. The invention further comprises lenses which are non-rigid permanently, that is, which do not undergo softening from an initial hard state. The term "non-rigid" in this application is intended to mean that a lens is capable of being deformed, rolled up, and even folded in half, without creasing or cracking the lens. Non-rigid lenses are capable of holding a given shape without requiring external support, but they are nonetheless to be distinguished from rigid lenses in which any effort to bend the lens can break it.

Many examples exist of materials, termed "hydrophilic", which are capable of being swollen and softened from an initial hard state to a non-rigid state by swelling and softening because of hydration, i.e. absorption of water. One of the most widely known hydrophilic materials is cross-linked 2-hydroxyethylmethacrylate, also known as HEMA or HEMA gel. Lenses which are homopolymers of HEMA are highly satisfactory in the present invention. Other satisfactory hydrophilic material is a homopolymer of 2,3-dihydroxypropylmethacrylate. The invention also includes lenses made of copolymers of a hydrophilic monomer, plus one or more other monomers. The other comonomer(s) may or may not be hydrophilic per se, so long as the resulting copolymerized material is hydrophilic and attains a softened, non-rigid state in water. Examples of such copolymers (with specific examples of weight ratios following in , parentheses) include:

HEMA/N-vinylpyrrolidone

HEMA/N-(1,1-dimethyl-3-oxobutyl)acrylamide/methacrylic acid

HEMA/N-vinylpyrrolidone/methylmethacrylate

HEMA/methacrylic acid

HEMA/2-ethoxyethyl methacrylate

HEMA/N-vinylpyrrolidone/methacrylic acid

HEMA/isobutyl methacrylate/methacrylic acid 2,3-dihydroxypropylmethacrylate/methyl methacrylate These polymers and copolymers are generally cross-linked with a minor amount less than 1 wt. % of a cross-linking agent such as divinyl benzene, 1,1,1-trimethylolpropane trimethacrylate, ethylene glycol dimethacrylate, ethylene bis (oxyethylene)dimethacrylate, ethylene dimethacrylate, or 2-ethyl-2-hydroxymethyl-1,3-propanediol trimethacrylate.

Examples of lens materials which are non-rigid without being hydrophilic include: silicone polymers and copolymers; cross-linked olefinic rubbers, such as poly(1-hexene); cross-linked silicone rubbers, such as poly(dimethyl siloxane-methylphenyl siloxane); fluorinated rubbers; and cross-linked alkyl (up to $C_{10}$) methacrylates, such as butyl methacrylate or a copolymer of butyl methacrylate and octyl methacrylate.

Procedures for polymerizing these materials, and for casting, molding, or cutting the polymerized material into lenses, are well known in the art. It is also known that the hydrophilic lenses can be made so that they absorb varying amounts of water in passing from the hard state to the non-rigid state. For example, HEMA materials are known which absorb 45%, 55%, and 70% water (by weight).

Figure 3:
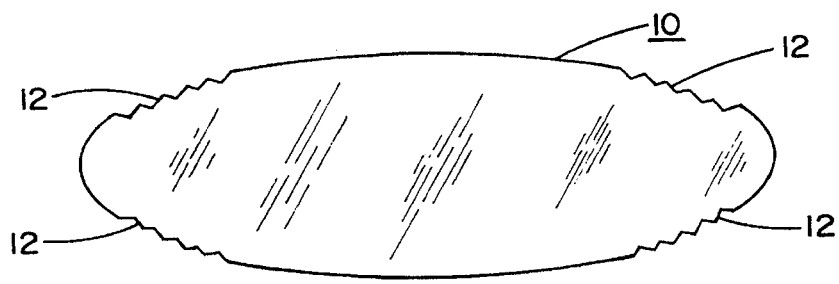
FIG. 3 is a side view of the invention.

In a preferred embodiment, the lens is circular in appearance with an elliptical cross-section, seen best in FIG. 3.

The present invention also extends to the manner in which the intraocular lens is held in position within the patient's capsular bag. In one embodiment, the lens is made in a thickness such that when the lens is in position (and fully swollen in equilibrium with the aqueous humor), the front and rear surfaces of the lens contact the front and rear capsular surfaces. In this way, contact between the capsule surfaces and lens surfaces can hold the lens in the desired position. Indeed, the lens having the elliptical cross-section shown in FIG. 3 can fill the posterior capsular bag, essentially completely, in which case proper positioning is also assured by contact between the outermost edge of the lens and the ciliary sulcus (the region in which the front and rear capsule surfaces come together).

Whether or not the lens itself extends to the ciliary sulcus, frictional engagement between the lens and the capsule surfaces can be enhanced by providing means for that purpose formed into the front, back, or both surfaces of the lens. The means can be roughened areas of any sort; preferred means include grooves in the form of arcs or complete circles formed in the lens surface. Spikes or similar sharp projections should be avoided, however, to minimize the risk of pain and injury to sensitive tissues. Grooves and equivalent engaging means can be easily formed, molded, or cut into the lens. When the lens material is hydrophilic, the forming is more easily carried out when the lens is in its hard state.

In another embodiment of this invention, an intraocular lens made of rigid material such as polymerized methyl methacrylate contacts the front and back surfaces of the posterior capsule, and has engaging means formed in at least one lens surface for engaging the adjacent capsular surface. More preferably, the engaging means is the only means associated with the lens for centering it in the eye. Thus, such a rigid lens can have the appearance of FIG. 3.

Figure 4:
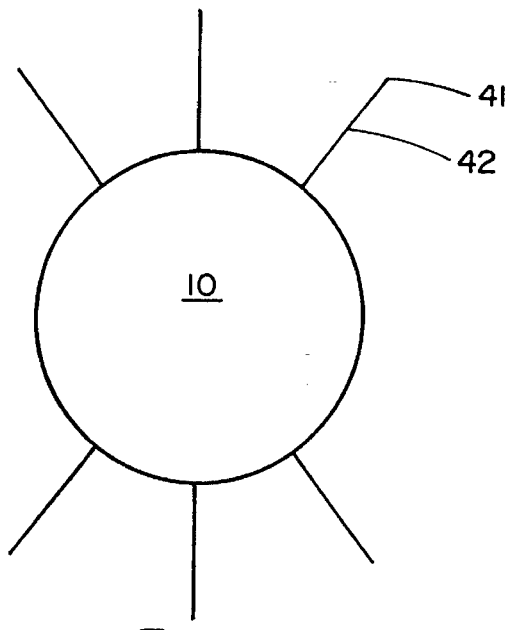
FIG. 4 is a front view of another embodiment of the invention.
Figure 5:
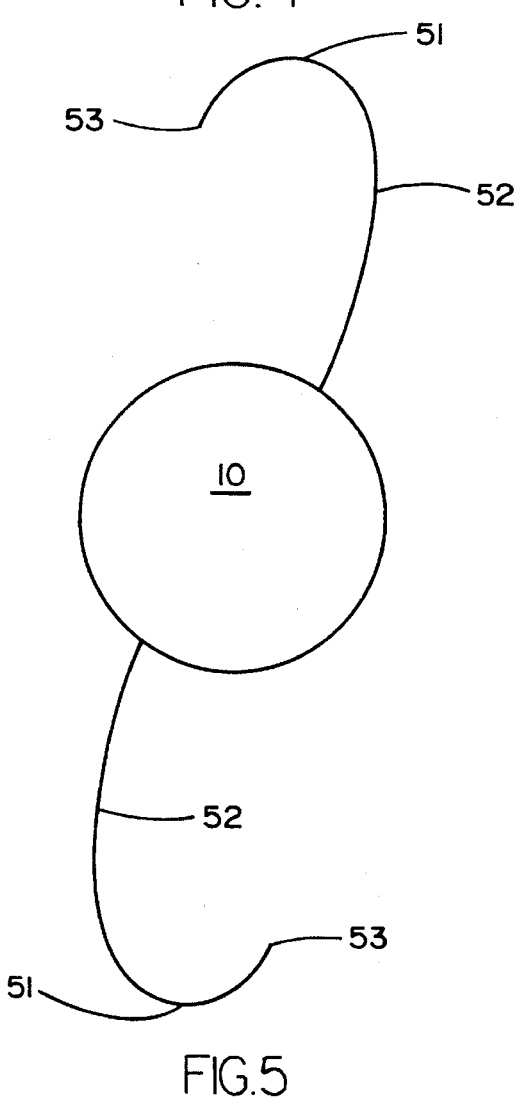
FIG. 5 is a front view of a further embodiment of the invention.

A non-rigid intraocular lens which does not fill the capsular bag can also be centered by structural means extending away from the lens body (defined as the portion of the lens which engages the front and rear of the capsular bag) such that the structural means engages the ciliary sulcus and centers the lens. The structural means can be present instead of, or in addition to, means formed in the lens surface itself. The structural means can comprise two or more legs attached to the lens body. The legs can extend generally radially from the lens body, as seen in FIG. 4 with the distal tips 41 of the legs 42 ending at the sulcus. The legs can be S-shaped or J-shaped, as shown in FIG. 5, wherein a curved portion 51 of each leg 52 engages the sulcus tangentially while the end 53 of the S or J does not engage the sulcus. It should be understood that the embodiments shown in the Figures are examples, and that other equivalent effective leg configurations can be employed such as modified J-shaped, C-shaped, reverse S-shaped, and closed loops in which both ends of a "leg" terminate at the lens body.

The legs can be molded as one piece with the lens body, or the end(s) of each leg are fitted into a small hole in the edge of the lens body or in a haptic zone extending from the edge of the lens body. The legs are preferably flexible, with a very thin diameter, and can be made of hydrophilic or non-hydrophilic material; a preferred material is polypropylene such as that sold under the trade name "Prolene" by Ethicon Pharmaceutical Company.

Figure 6:
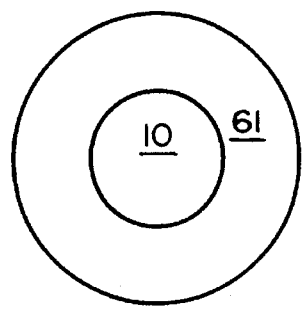
FIG. 6 is a front view of yet another embodiment of the invention.
Figure 7:
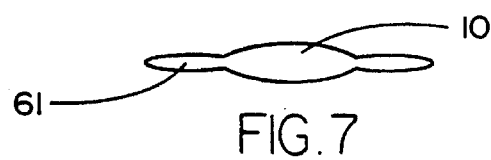
FIG. 7 is an edge view of the embodiment of FIG. 6.
Figure 8:
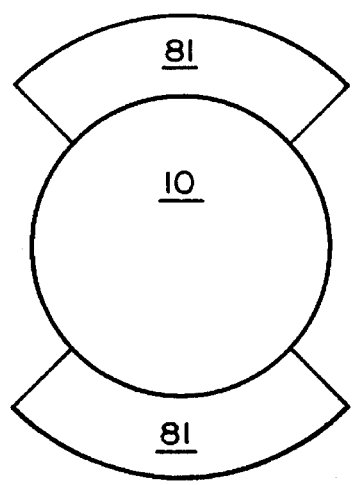
FIG. 8 is a front view of another embodiment of the invention.
Figure 9:
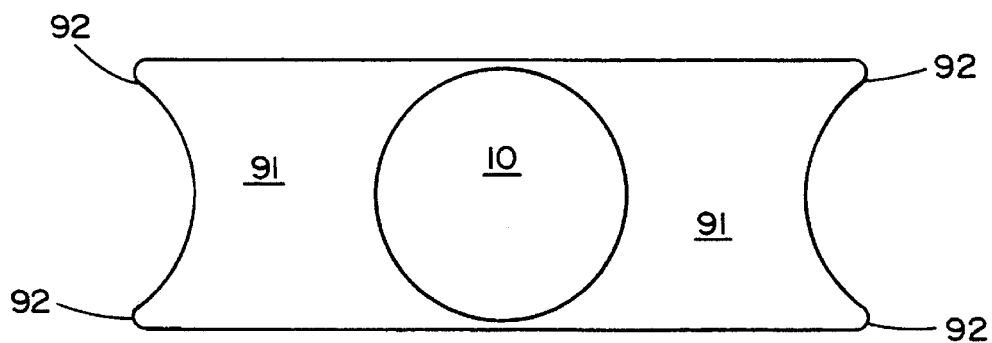
FIG. 9 is a front view of yet another embodiment of the invention.

Alternatively, the structural means can comprise one or more haptic zones, by which is meant a web of material extending from the lens body toward or to the sulcus without engaging the front or back surface of the posterior capsule. The haptic can be a circular region 61 as seen in FIGS. 6 and 7, extending all the way around the lens body. Alternatively, it can comprise two or more spaced-apart arcuate sectors 81 of a circle, as seen in FIG. 8. As another alternative, it can comprise two or more tab-like areas 91 as seen in FIG. 9, having angled corners 92 which engage the sulcus. Other equivalent means will be apparent to the skilled practitioner. The haptic can be made of rigid material, such as polymerized methyl methacrylate, or preferably of non-rigid material integral with the lens body. Preferably, the haptic zones are located so that the lens can take as small a shape as possible as it is about to be inserted into the eye. In this way, the incision which the surgeon must make in the cornea is as small as possible. When the haptic comprises a plurality of tabs as in FIGS. 8 and 9, they are preferably located so that a non-rigid lens can be folded across a diameter prior to insertion, or located along the same diameter of an initially hard hydrophilic lens so that the lens can be inserted along that diameter. More preferably, the tabs 81 and 91 will not be wider than the diameter of the lens body.

A lens in accordance with any of the embodiments of this invention is made to fit the dimensions of the patient's capsular bag. Generally, the diameter of the capsular bag is about 12–14 millimeters: lenses having structure which engages the sulcus are made to equal or slightly exceed that dimension so that the structure exerts some force to hold the lens in position. The practitioner will also ascertain the approximate front-to-back distance, so that a lens thick enough to engage both capsular surfaces can be made. Of course, where the lens is hydrophilic and is designed to be hard when inserted, the lens will have been made in a size which takes into account the degree of swelling which the lens will undergo in the eye. The lens is most preferably made of hydrophilic material having the maximum possible degree of expansion on hydration, and is inserted in the dry state. In this way, the size of the incision needed is minimized.

The lenses of the present invention are inserted into the eye of a recipient in the manner customarily employed in this art. When the lens is made of hydrophilic material and is in the dry state, the lens can be inserted through an incision in the cornea which is smaller than the size the lens will attain after it has swollen in the capsular bag. Alternatively, when the lens is made of soft, non-hydrophilic material, or is hydrophilic and has already been swollen and softened, it can be folded over on itself or even rolled up, to a shape with a cross-section that requires an incision in the cornea smaller than the size of the unfolded lens. The lens is then opened and positioned after it has been placed in the capsular bag.

Figure 2:
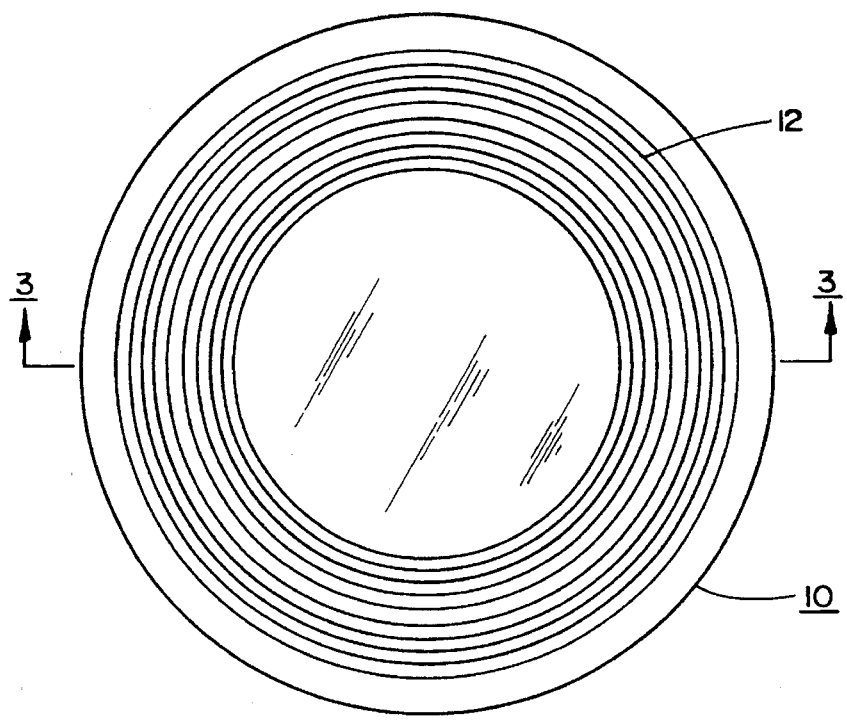
FIG. 2 is a plan view of the invention.

Referring to FIGS. 1–3, the lens 10 of the invention comprises a lens made of soft material, HEMA, with a water uptake of 45%, 55%, or 70%. The lens is round with concentric grooves 12 cut into marginal peripheral areas on both sides of the lens. The cutting and shaping of the lens 10 is done with dry HEMA, at a reduction in size proportional to expansion of the type of HEMA used after water uptake, of the desired size that is to fill the capsular bag 14 (see FIG. 1) as shown in full lines. The lens is inserted dry through a hole 18 trephined in the center of the forward wall 20 of the capsular bag 14. Uptake of aqueous humor of the eye softens and expands lens 10 from its original insertion size as shown in broken lines to fill bag 14. Grooves 12 frictionally engage the inside walls of the capsule that are naturally rough to firmly hold the lens in place without additional clips, loops, and/or staves and sutures (not shown). A hole 20 can also be optionally trephined in the center of the rear wall 20 to allow for the passage of light through the lens to the retina of the eye. Posterior holes 18 and 20 are respectively 4 to 6 mm. and 3 to 4 mm. in diameter.

If the lens should for any reason become dislodged, no damage to the retina should occur because the lens is round, soft and has no clips or loops or other external apparatus for holding the lens in position.

The lens can be made with any optical correcting surface desired, including embodiments in which each surface can be convex, concave, plano, or aspheric. The lens material can also contain an ultraviolet-radiation absorbing compound.

This particular invention is not necessarily limited to cataract patients. Another possibility would be the correction of high myopia or hyperopia. Lens curves can be properly calculated so they correct for the best possible visual acuity. Since the implanted lens has a better clarity than the present natural crystalline lens, much better acuity can be achieved especially with aspheric surfaces. The lenses can also be used to correct astigmatism. A cylinder can be ground on one or both surfaces. The axis is aligned with two locating holes or pins through the anterior capsule. Once the cylinder axis of the lens is properly aligned with respect to the capsule, it can be fastened through the membrane by tacking the detached retina to the globe with a laser in a manner analogous to that used in retina surgery.

What is claimed is:

1. In an artificial intraocular lens for surgical implantation to replace a damaged natural lens in an otherwise functional eye of a patient, the improvement which comprises:

said artificial lens having a cross sectional dimension less than that of the natural lens, and being composed of a dry, solid hydrophilic material capable of hydration by the natural fluid present in the eye to expand after implantation to provide an optically correct lens;

to thus improve the vision of the patient.

2. In a method for the surgical implantation of an artificial intraocular lens to replace a damaged natural lens in an otherwise functional eye of a patient, the improvement which comprises: implanting an artificial lens having a minimum diameter less than that of the natural lens and being composed of a dry, solid hydrophilic material capable of hydration by the natural fluid present in the eye to expand after implantation to provide an optically correct lens;

said implantation of the dry lens being made through an incision of minimal width corresponding substantially to the diameter of said dry lens.

3. A lens according to claim 2 wherein said lens is made of flexible, non-hydrophilic, physiologically inert material.

4. An artificial intraocular lens of claim 1, having means for supporting said lens in the posterior chamber of the eye.

5. An artificial lens of claim 1 wherein the hydrophilic material is hydroxyethyl methacrylate.

6. An artificial intraocular lens of claim 4 wherein the diameter of the optical portion of the lens is less than 6 mm.

7. An artificial intraocular lens of claim 4 wherein the diameter of the optical portion of the lens is less than 5 mm.

8. The method of claim 2 wherein the hydrophilic material is hydroxyethyl methacrylate.

9. The method of claim 2 wherein the artificial intraocular lens is positioned within the posterior capsule of the eye.

10. The method of claim 9 wherein the optical portion of the artificial intraocular lens is less than 5 mm.

11. The method of claim 9 wherein the optical portion of the artificial intraocular lens is less than 6 mm.

12. The method of claim 10 wherein the artificial intraocular lens is a hydrophilic material comprising hydroxyethyl methacrylate.

13. The method of claim 11 wherein the artificial intraocular lens is a hydrophilic material comprising hydroxyethyl methacrylate.

14. A lens according to claim 1 or 2 being formed of a non-rigid, non-hydrophilic material taken from the group consisting of silicone polymers and copolymers, cross-linked olefinic rubbers, fluorinated rubbers; and cross-linked alkyl (up to $C_{10}$) methacrylates.

15. A lens according to claim 1 or 2 which comprises a plastic circular body means for emplacement within the posterior capsule when said body means is dry and contracted, and which is adapted to expand in place when softened by uptake of aqueous humor in the posterior capsule.

16. A lens according to claim 14 which is in a non-rigid state before insertion thereof into the posterior capsule.

17. A lens according to claim 1 or 2 wherein said lens is a polymer of 2,3-dihydroxypropylmethacrylate and one or more comonomers.

18. A lens according to claim 1 or 2 which is made of a copolymer of HEMA and one or more comonomers.

19. A lens according to claim 1 or 2 wherein said lens is a copolymer of HEMA and N-vinylpyrrolidone.

20. A lens according to claim 1 or 2 wherein said lens is a copolymer of HEMA and N-(1,1-dimethyl-3-oxobutyl)acrylamide and methacrylic acid.

21. A lens according to claim 1 or 2 wherein said lens is a copolymer of HEMA and N-vinylpyrrolidone and methyl methacrylate.

22. A lens according to claim 1 or 2 wherein said lens is a copolymer of HEMA and methacrylic acid.

23. A lens according to claim 1 or 2 wherein said lens is a copolymer of HEMA and 2-ethoxyethylmethacrylate.

24. A lens according to claim 1 or 2 wherein said lens is a copolymer of HEMA, N-vinylpyrrolidone and methacrylic acid.

25. A lens according to claim 1 or 2 wherein said lens is a copolymer of HEMA, isobutyl methacrylate and methacrylic acid.

26. A lens according to claim 1 or 2 wherein said lens is a copolymer of 2,3-dihydroxypropylmethacrylate and one or more comonomers.

27. A lens according to claim 1 or 2 wherein said lens is a copolymer of 2,3-dihydroxypropylmethacrylate and methyl methacrylate.

28. An intraocular lens as described in claim 1 or 2 wherein said plastic hydrophilic circular body means comprises a HEMA with 45% liquid uptake.

29. An intraocular lens as described in claim 1 or 2 wherein said plastic hydrophilic circular body means comprises a HEMA with 55% liquid uptake.

* * * * *